United States Patent [19]

Johnson et al.

[11] Patent Number: 5,290,815
[45] Date of Patent: Mar. 1, 1994

[54] TREATMENT OF INFLAMMATION AND ALLERGY

[75] Inventors: Malcolm Johnson, Orwell; Clifford J. Whelan, Buntingford, both of England

[73] Assignee: Glaxo Group Limited, London, England

[21] Appl. No.: 799,001

[22] Filed: Nov. 25, 1991

Related U.S. Application Data

[63] Continuation of Ser. No. 578,353, Sep. 6, 1990, abandoned.

[30] Foreign Application Priority Data

Sep. 7, 1989 [GB] United Kingdom ............... 8920235
May 29, 1990 [GB] United Kingdom ............... 9011940

[51] Int. Cl.$^5$ .............................. A61K 31/135
[52] U.S. Cl. .................... 514/651; 514/851
[58] Field of Search ................ 514/651, 851

[56] References Cited

FOREIGN PATENT DOCUMENTS 2140800 12/1984 United Kingdom .

OTHER PUBLICATIONS

The Merck Manual, 10th ed., 1961, pp. 10–13 & 1306–1309.
Br. J. Pharmac, (1980) 71, 663–667, Butchers et al. I
Am. Rev. Resp. Dis., (1985) 132 986–992, Howarth et al.
Br. J. Pharmac, (1987) 92, 745P, Butchers et al. II Doctor, 1989, Feb. 23, 1973.
Hospital Doctor, 1989 C9 (10), 35 Mims Magazine 1989, Mar. 15, 16.
Pulse, 1989, Oct. 14, 1986, Deuchar Doctor, 1989, Nov. 16, 1936.
S. T. Holgate, Postgrad. Med. J., 64, 82–95 (1989).
Folkerts, et al., Agents & Actions, 23, 94–96 (1988).
Aoki et al., J. Physiol, 394, 130p (1987).
Erjefalt et al., Acta, Physiol. Scand., 128, 653–654 (1986).
Issekutz et al., Lab. Invest., 42, 310–317 (1980).
Issekutz et al., Lab. Invest., 45, 435–441 (1981).
Butchers et al., Br. J. Pharmac., 67, 23–32 (1979).

Primary Examiner—Leonard Schenkman
Attorney, Agent, or Firm—Morgan & Finnegan

[57] ABSTRACT

The present invention provides a new medical use for the phenethanolamine compound 4-hydroxy-$\alpha^1$-[[[6-(4-phenylbutoxy)hexyl]amino]methyl]-1,3-benzenedimethanol and physiologically acceptable salts and solvates thereof in the treatment of inflammation, allergy and allergic reaction.

3 Claims, 4 Drawing Sheets

TREATMENT OF INFLAMMATION AND ALLERGY

This is a continuation of copending application Ser. No. 07/578,353, filed on Sep. 6, 1990, now abandoned.

This invention relates to a new medical use for the phenethanolamine compound 4-hydroxy-$\alpha^1$-[[[6-(4-phenylbutoxy)hexyl]amino]methyl]-1,3-benzenedimethanol, physiologically acceptable salts and solvates thereof and pharmaceutical compositions containing them which are disclosed in published UK Patent Specification No. 2140800, in the treatment of inflammation, allergy, and allergic reaction.

Acute inflammation is the result of a number of processes including the activation of inflammatory cells and their accumulation in tissues; the local release of pro-inflammatory and chemotactic mediators; and vascular permeability changes which lead to plasma protein extravasation (PPE) and oedema formation.

One particular clinical condition with which inflammatory processes are associated is bronchial asthma. As reported by S. T. Holgate, *Postgrad.Med.J.*, 64, 82–95 (1988), bronchial asthma is a multifactorial disease characterised by episodic bronchoconstriction, airway hyper-reactivity, inflammation and mucus abnormalities.

To date, bronchial asthma has been treated by combination therapy, using selective $\beta_2$-stimulants such as salbutamol to control bronchospasm and steroidal drugs such as beclomethasone dipropionate to control the inflammatory condition. $\beta_2$-adrenoreceptor agonists including salbutamol have been reported to exhibit inhibitory effects on inflammatory mediator release (see, for instance, P. R. Butchers et, al., *Br J Pharmac.*, 71, 663–667 (1980) and P. H. Howarth et al., *Am. Rev Resp. Dis.*, 132, 985–992 (1985)), however, currently available $\beta_2$-adrenoreceptor agonists are not widely recognised as having significant clinical anti-inflammatory properties.

Published UK Patent Specification No. 2140800 discloses compounds which may be represented by the formula (I)

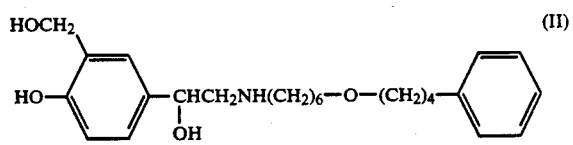

wherein
m is an integer from 2 to 8 and
n is an integer from 1 to 7 with the proviso that the sum total of m+n is 4 to 12;
Ar represents a phenyl group optionally substituted by one or two substituents selected from halogen atoms, $C_{1-3}$alkyl or $C_{1-3}$alkoxy groups, or by an alkylenedioxy group of formula —O(CH$_2$)$_p$O— where p is 1 or 2; and
$R^1$ and $R^2$ each represents a hydrogen atom or $C_{1-3}$alkyl group with the proviso that the sum total of carbon atoms in $R^1$ and $R^2$ is not more than 4;
and physiologically acceptable salts and solvates (e.g. hydrates) thereof.

Suitable physiologically acceptable salts of the compounds of general formula (I) include acid addition salts derived from inorganic and organic acids, such as hydrochlorides, hydrobromides, sulphonates, phosphates, maleates, tartrates, citrates, benzoates, 4-methoxybenzoates, 2- or 4-hydroxybenzoates, 4-chlorobenzoates, p-toluenesulphonates, methanesulphonates, asorbates, salicylates, or tricarballylates, hydroxy-naphthalenecarboxylates e.g. 1-hydroxy- or 3-hydroxy-2-naphthalenecarboxylates, or oleates.

Particularly preferred salts, having a very low solubility in water, include diphenyl acetates, 4,4'-methylenebis 3-hydroxy-2-naphthalenecarboxylates, and 1-hydroxy- and 3-hydroxy-2-naphthalenecarboxylates.

A preferred compound of formula (I) for use according to the present invention is 4-hydroxy-$\alpha^1$-[[[6-(4-phenylbutoxy)hexyl]amino]methyl]-1,3-benzenedimethanol, which may be represented by the formula (II)

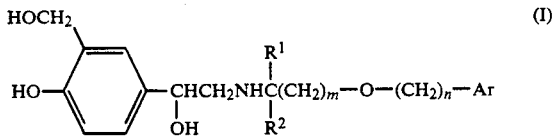

and its physiologically acceptable salts and solvates.

The compound of formula (II), also referred to herein as salmeterol, is preferably administered in the form of its 1-hydroxy-2-naphthalenecarboxylate salt.

The compounds disclosed in the aforementioned patent specification are described as selective $\beta_2$-adrenoreceptor agonists having a long duration of action which are particularly useful in the treatment of diseases associated with reversible airways obstruction, such as asthma and chronic bronchitis.

We have now found that contrary to all previous findings for $\beta_2$ adrenoreceptor agonists, the compounds of formula (I) exhibit a significant anti-inflammatory activity in vivo over a prolonged period such that the compounds of formula (I) are effective in the treatment of the inflammatory component of bronchial asthma. Thus the compound of formula (II) is of use in the treatment of inflammation, allergy and allergic reaction. The anti-inflammatory activity of the compound of formula (II) was demonstrated by its inhibitory effect on zymosan-induced granulocyte accumulation and plasma protein extravasation (PPE) in guinea-pig skin. In particular, the compound of formula (II) has been shown to be a potent and long-acting inhibitor of inflammatory and spasmogenic mediator release from human lung, of inflammatory cell infiltration and accumulation, and of vascular permeability and plasma protein extravasation in guinea pig lung in vivo.

By virtue of its anti-inflammatory activity, the compound of formula (II) may be used in the treatment of a mammal, including man, suffering from pulmonary inflammation including alveolar inflammation and inflammation of the respiratory airways. In particular, the compound of formula (II) is useful in the treatment of inflammation associated with pulmonary diseases such as asthma and chronic bronchitis, emphysema, cystic fibrosis and adult respiratory distress syndrome (ARDS).

Additionally, the compound of formula (II) may be used in the treatment of a mammal, including man, suffering from an allergy or allergic reaction such as allergic rhinitis, contact dermatitis, allergic conjunctivitis and the like or an inflammatory condition such as episcleritis, tendinitis, rheumatoid spondylitis, osteoarthritis, gouty arthritis and other arthritic conditions.

The compound of formula (II) is particularly useful in the treatment of inflammatory and allergic skin diseases such as, for example, urticaria, psoriasis, eczema and atopic dermatitis.

The compound of formula (II) may also be used in the treatment of a mammal, including man, suffering from inflammation of the gastrointestinal tract. Such conditions may be for example, ulcerative colitis, Crohn's disease, damage caused by non-steroidal drugs, and inflammatory bowel disease.

According to one aspect of the invention we therefore provide a therapeutic agent comprising as active ingredient the compound of formula (II) or a physiologically acceptable salt or solvate thereof for use in treating, relieving or preventing the effects of inflammation, allergy, or allergic reaction.

In an alternative or further aspect the invention provides a method of treatment of a mammal, including man, suffering from or susceptible to the effects of inflammation, allergy or allergic reaction which comprises administering an effective amount of the compound of formula (II) or a physiologically acceptable salt or solvate thereof.

It will be appreciated that whilst the compound of formula (II) will primarily be of use in the alleviation of established symptoms, prophylaxis is not excluded.

In a further aspect, the invention provides the compound of formula (II) or a physiologically acceptable salt or solvate thereof for use in the manufacture of a medicament for treating relieving or preventing the effects of inflammation, allergy, or allergic reaction.

The anti-inflammatory activity of salmeterol in the lung was assessed by investigating the effect of the drug on inflammatory mediator release in human lung tissues in vitro, and on inflammatory cell infiltration and accumulation, and vascular permeability and plasma protein extravasation in the airway lumen of the guinea-pig in vivo (see Example 1, below).

The anti-inflammatory activity of salmeterol in the skin was assessed by investigating the effect of the drug on granulocyte accumulation and granulocyte-dependent and independent vascular permeability (see Example 2, below).

Thus, in an alternative or further apsect the invention provides the compound of formula (II) or a physiologically acceptable salt or solvate thereof for use in treating, relieving or preventing a disease involving inflammatory cell accumulation in the lungs.

The present invention provides a method of treatment of a mammal, including man, suffering from the late asthmatic reaction or suffering from late-phase asthma which comprises in each case administering an effective amount of 4-hydroxy-$\alpha^1$-[[[6-(4-phenylbutoxy)hexyl]amino]methyl]-1,3-benzenedimethanol or a physiologically acceptable salt or solvate thereof.

Additionally the invention provides the compound of formula (II) or a physiologically acceptable salt or solvate thereof for use in treating, relieving or preventing a disease involving increased vascular permeability and plasma protein extravasation in the lungs.

The invention further provides the compound of formula (II) or a physiologically acceptable salt or solvate thereof for use in treating, relieving or preventing a disease involving increased vascular permeability in the skin.

The invention still further provides the compound of formula (II) or a physiologically acceptable salt or solvate thereof for use in treating, relieving or preventing a disease involving increased vascular permeability in the skin.

As used herien, the term "increased vascular permeability" intended to refer to elevated levels of vascular permeability in with respect to those generally observed in a healthy individual.

While it is possible for the compound of formula (II) to be administered alone as the raw chemical, it is preferable to present the active ingredient as a pharmaceutical formulation. Formulations of the compound of formula (II) for use according to the invention, both for veterinary and for human medical use, comprise the active compound together with one or more pharmaceutically acceptable carriers and optionally any other therapeutic ingredients. The carriers must be pharmaceutically acceptable in the sense of being compatible with the other ingredients of the formulation and not deleterious to the recipient thereof. The other therapeutic ingredients may include analgesics, such as aspirin or codeine, anti-pyretics, or other anti-inflammatories.

The compound of formula (II) for use according to the invention may be formulated in a conventional manner for administration by any convenient route, for example for administration by inhalation or insufflation, or for oral buccal, parenteral, topical (including nasal) or rectal administration.

For administration by inhalation the compound for use according to the invention is conveniently delivered in the form of an aerosol spray presentation from pressurised packs, with the use of a suitable propellants such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compound of formula (II) may take the form of a dry powder composition, for example a powder mix of the compound and a suitable powder base such a lactose or starch. The powder composition may be presented in unit dosage form in, for example, capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in a conventional a manner.

The compound of formula (II) may be formulated for parenteral administration. Formulations for injections may be presented in unit form in ampoules, or multidose containers with an added preservative. The compositions may take such forms as suspensions, solutions or emulsions in oily or aqueous vehicles, and may contain formulatory agents such as suspending, stabilising and or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous oily base, generally with the addition of suitable thickening agents and or solvents. For nasal application, the composition may take the form of a spray, formulated for example as an aqueous solution or suspension or as an aerosol with the use of a suitable propellant.

The compound of formula (II) may also be formulated in rectal compositions such as suppositories or retention enemas, e.g. containing conventional suppository bases such as cocoa butter or other glycerides.

Where pharmaceutical compositions are described above for oral, buccal, rectal or topical administration, these may be presented in a conventional manner associated with controlled release forms.

A proposed daily dosage of active compound for the treatment of man is 0.0005 mg to 100 mg, which may be conveniently administered in one or two doses. The precise dose employed will of course depend on the age and condition of the patient and on the route of administration. Thus a suitable dose for administration by inhalation is 0.0005 mg to 10 mg, for oral administration is 0.02 mg to 100 mg, and for parenteral administration is 0.001 mg to 2 mg.

The following are examples of suitable formulations for use in invention. The term "active ingredient" is used herein to represent the compound of formula (II).

TABLETS

These may be prepared by the normal methods such as wet granulation or direct compression.

| A. Direct Compression | mg/tablet |
| --- | --- |
| Active ingredient | 2.0 |
| Microcrystalline Cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

| B. Wet Granulation | mg/tablet |
| --- | --- |
| Active ingredient | 2.0 |
| Lactose BP | 151.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulated. After drying, the granules are then compressed into tablets using 7 mm diameter punches. Tablets of other strengths may be prepared by altering the ratio of active ingredient to lactose or the compression weight and using punches to suit.

Injection for Intravenous Administration

| | mg/ml |
| --- | --- |
| Active ingredient | 0.5 mg |
| Sodium Chloride BP | as required |
| Water for injection BP to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under acceptable conditions. The solution may be packed under an inert atmosphere of nitrogen or other suitable gas.

Metered Dose Pressurised Aerosol

| A. Suspension Aerosol | mg/metered dose | per can |
| --- | --- | --- |
| Active ingredient micronised | 0.100 | 26.40 mg |
| Oleic Acid BP | 0.010 | 2.64 mg |
| Trichlorofluormethane BP | 23.64 | 5.67 g |
| Dichlorodifluoromethane BP | 51.25 | 14.70 g |

The active ingredient is micronised in a fluid energy mill to a fine particle size range, The oleic acid is mixed with the trichlorofluormethane at a temperature of 10°–15° C. and the micronised drug is mixed into the solution with a high shear mixer. The suspension is metered into aluminium aerosol cans and suitable metering valves, delivering 85 mg of suspension are crimped onto the cans and the dichlorodifluoromethane is pressure filled into the cans through the valves.

| B. Solution Aerosol | mg/metered dose | per can |
| --- | --- | --- |
| Active ingredient | 0.100 | 24.0 mg |
| Ethanol BP | 7.500 | 1.80 g |
| Trichlorofluoromethane BP | 18.875 | 4.53 g |
| Dichlorodifluoromethane BP | 48.525 | 11.65 g |

Oleic acid BP, or a suitable surfactant e.g. Span 85 (sorbitan trioleate) may also be included.

The active ingredient is dissolved in the ethanol together with the oleic acid or surfactant if used. the alcoholic solution is metered into suitable aerosol containers followed by the trichlorofluoromethane. Suitable metering valves are crimped onto the containers and dichlorodifluoromethane is pressure filled into them through the valves.

The following examples illustrate the studies demonstrating the potent and long-acting anti-inflammatory activity effect of salmeterol (the compound of formula (II)) in the lung and in the skin.

The following abbreviation are used in: —LPS—lipopolysaccharide; PAF—platalet activating factor; BALF—bronchoalveolar fluid; PPE—plasma protein extravasation; PMN—guinea pig peritoneal neutrophil.

EXAMPLE 1

ANTI-INFLAMMATORY ACTIVITY IN THE LUNG

(i) Inflammatory Mediator Release

The effect of $\beta_2$-adrenoreceptor agonists on inflammatory mediator release was evaluated using the method of Butchers et al *Br. J. Pharmac.*, 67,23–32 (1979).

Briefly, human lung fragments were sensitised by incubation overnight at 20° C. in serum from an allergic donor. The lung fragments were then pre-incubated with varying concentrations (0.3–300 nM) of $\beta_2$-adrenoreceptor agonists for 30 min. before being challenged with specific antigen. The supernatants were assayed for histamine, leukotriene $C_4$ and $D_4$, and prostaglandin $D_2$ release by radio-immunoassay (Serotec, UK). Inhibition of mediator release was calculated as described by Butchers et al (1979) supra.

To compare the duration of action of $\beta_2$-agonists, sensitised human lung fragments were pre-incubated with a single concentration of compound sufficient to cause just maximum inhibition of histamine release. The fragments were then washed and incubated in a large volume of Tyrode's solution at 37° C. Aliquots were removed at varying time intervals (0–20 h), challenged with antigen and mediator release measured as described above.

Salmeterol (0.2–100 nM) caused a concentration-dependent inhibition of the release of histamine, leukotriene $C_4/D_4$ and prostaglandin $D_2$ from human lung fragments with an $IC_{50}$ of 0.9–3 nM. Salbutamol in the same experiments had an $IC_{50}$ of 11–52 nM.

Figure 1:
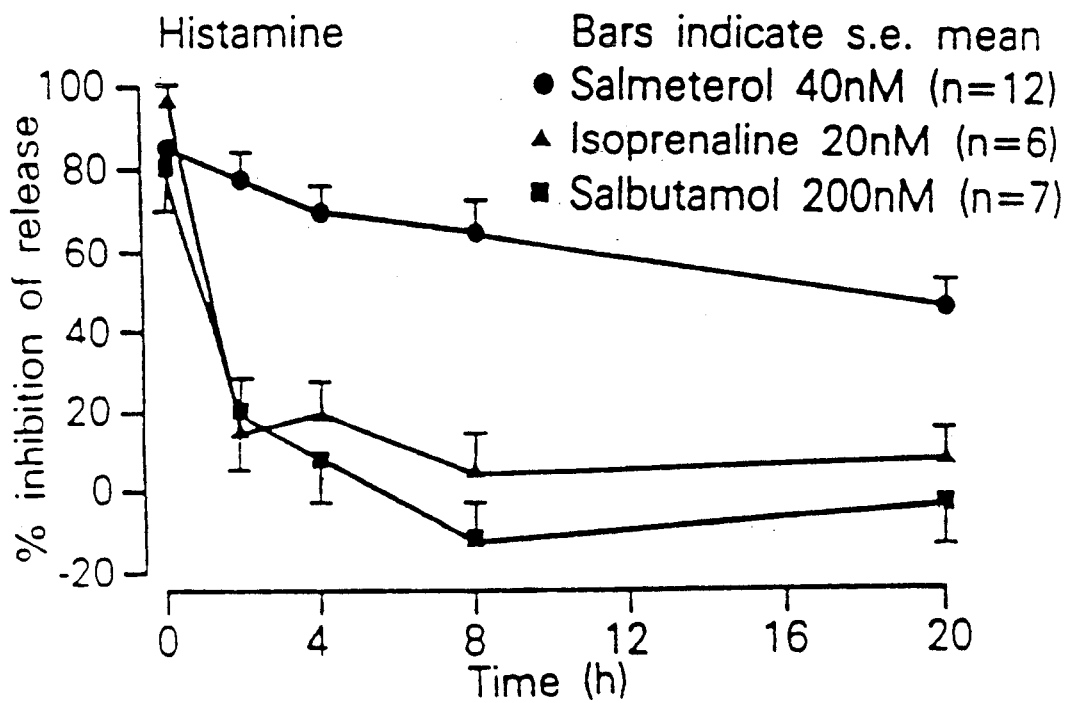
FIG. 1A and FIG. 1B show the duration of action of beta adrenoceptor agonists as inhibitors of mediator release from human lung
Figure 1:
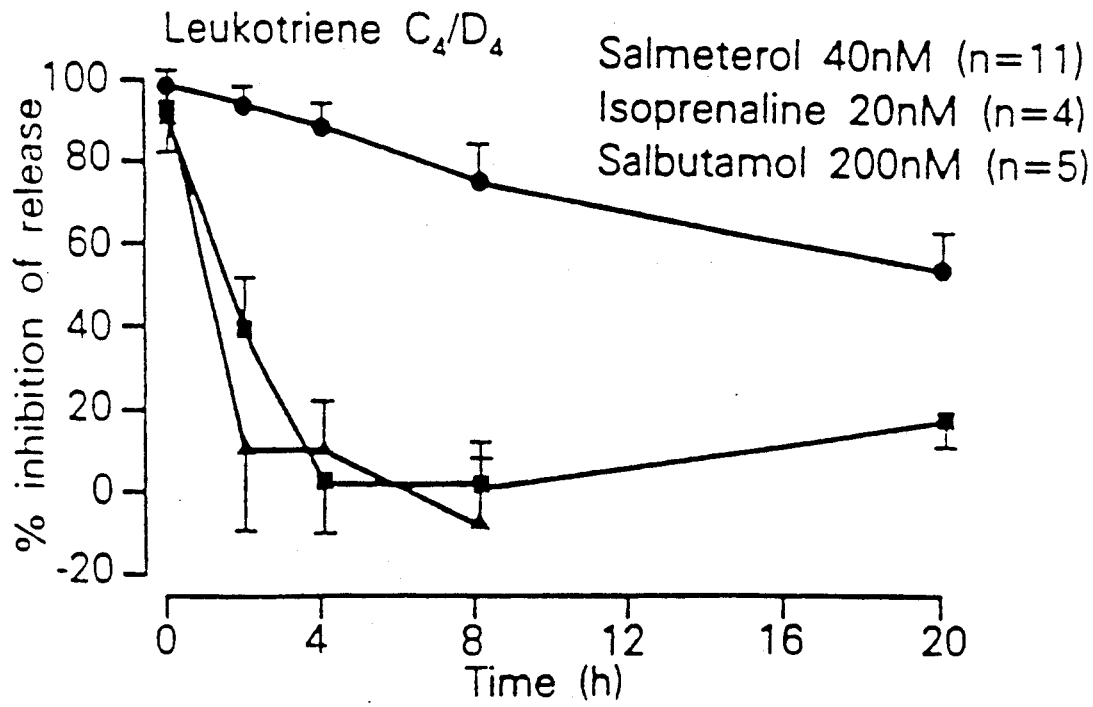

Inhibition of histamine and leukotriene release by salmeterol (40 nM) was sustained, significant ($p<0.005$) inhibitory activity still being observed after 20 h (FIG. 1). In contrast, the effect of equipotent concentration of isoprenaline (20 nM) and salbutamol (200 nM) was poorly maintained, with loss of inhibitory activity within 2–4 h.

(ii) Inflammatory cell Accumulation

The method of evaluating the effects of $\beta_2$-adrenoreceptor agonists on inflammatory cell infiltration into the lung was based on the techniques of Folkerts et al *Agents and Actions*, 23, 94–96 (1988) and Aoki et al *J. Physiol.*, 394, 130p (1987).

Briefly, guinea-pigs (male Dunkin Hartley, 300–400 g) were exposed to an aerosol of 100 $\mu g.ml^{-1}$ *E.coli* lipopolysaccharide (LPS; 026:B6, Sigma Ltd) or 100 $\mu g.ml^{-1}$ platelet activating factor (PAF; Sigma Ltd.) for 10 min. Four hours after LPS and 24 hours after PAF, the lungs of the animals were lavaged twice with 10 ml heparinised (10 $U.ml^{-1}$) phosphate-buffered saline at 37° C. The total leukocyte count of the bronchoalveolar lavage fluid (BALF) recovered was determined. A cytospin preparation was prepared from the BALF, fixed with methanol, stained with Wright's stain and a differential leukocyte count was carried out.

Exposure of guinea-pigs to LPS (100 $\mu g.ml^{-1}$) resulted in an increase in the BALF neutrophil count from $3.8\pm1.2\times10^3$ cells.$ml^{-1}$ to $141.3\pm33.3\times10^3$ cells.$ml^{-1}$, 4 hours after challenge. Salmeterol (0.1 mg.$ml^{-1}$) aerosol, 30 min. prior to challenge substantially reduced the LPS-induced neutrophil accumulation ($46.8\pm9.1\times10^3$ cells.$ml^{-1}$).

Figure 2:
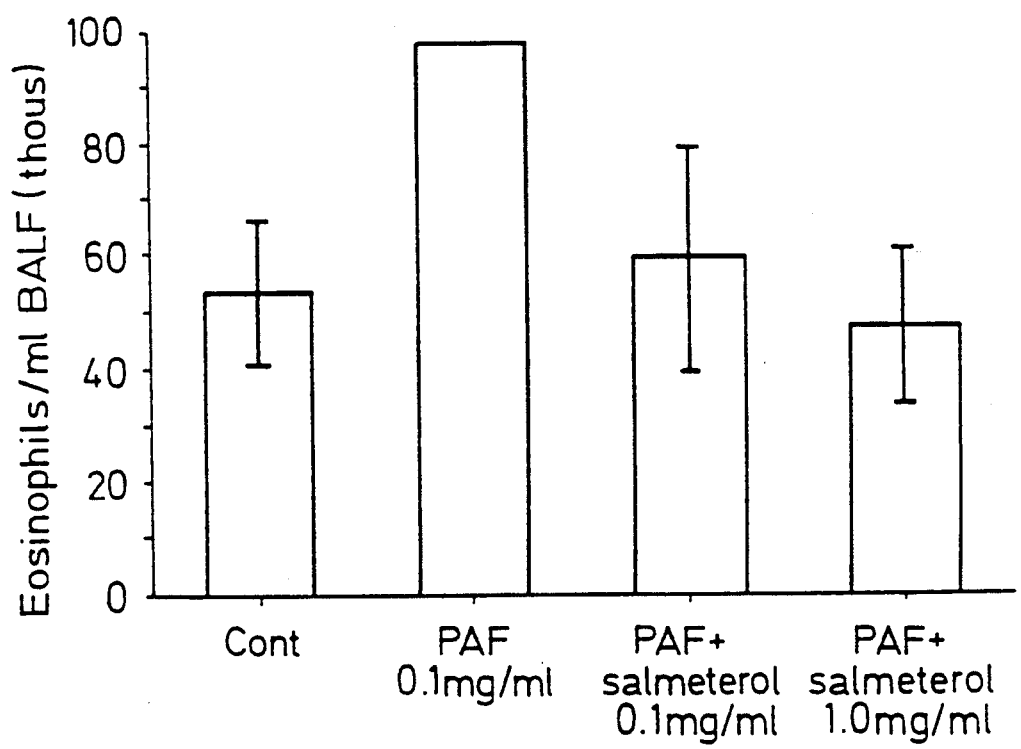
FIG. 2 shows inhibition of PAF-induced eosinophil accumulation in guinea pig lungs by salmeterol aerosols.

PAF (100 $\mu g.ml^{-1}$) increased the BALF eosinophil count from $53.3\pm12.5\times10^3$ cells. $ml^{-1}$ to $97.7\pm18.8\times10^3$ cells.$ml^{-1}$, 24 hours after challenge. Salmeterol, administered by inhalation at 0.1 mg.$ml^{-1}$ 30 min prior to challenge, completely abolished PAF-induced eosinophil infiltration (FIG. 2 shows the inhibition of PAF-induced eosinophil acculation in guinea pig lungs by salmeterol aerosols) into the bronchial lumen (eosinophil count: $59.2\pm19.8\times10^3$ cells.$ml^{-1}$).

(iii) Vascular Permeability and Plasma Protein Extravasation

The method of evaluating the effects of $\beta_2$-adrenoreceptor agonists on vascular permeability and plasma protein extravasation was adapted from the technique of Erjefalt et al *Acta. Physiol. Scand.*, 128, 653–654 (1986).

Briefly, guinea-pigs (male Dunkin Hartley, 300–400 g) were given an intracardiac injection of iodinated human serum albumin (0.5 $\mu Ci$) in heparinised saline (10 $U.ml^{-1}$). Animals were then exposed to an aerosol of histamine (0.5 mg.$ml^{-1}$) generated by a Devilbiss nebuliser for 30 sec, followed by a further 30 sec exposure to the atmosphere in the chamber. Thirty minutes after histamine challenge, a blood sample was taken and the lungs lavaged twice with 10 ml heparinised (10 $U.ml^{-1}$) phosphate-buffered saline at 37° C. The radioactivity in both an aliquot of plasma and in a 5 ml sample of the pooled bronchoalveolar lavage fluid (BALF) was measured. Plasma protein extravasation (PPE; $\mu l$ plasma.$ml^{-1}$ BALF) was calculated. $\beta_2$-adrenoreceptor agonists were administered by aerosol as described by Ball et al *Br. J. Pharmac.*, 90. 150P (1987), or by the oral route, at timed intervals before histamine challenge.

Figure 3:
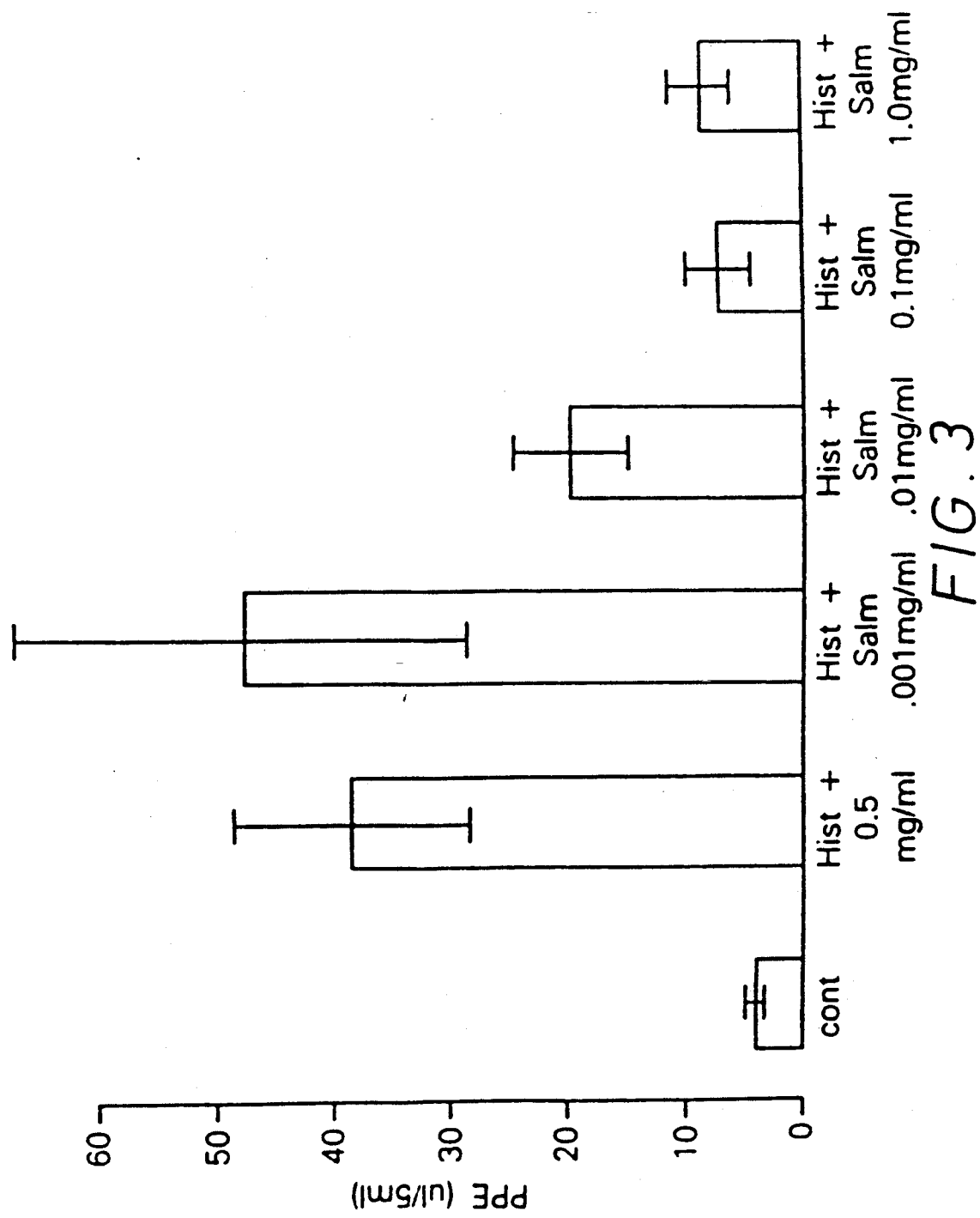
FIG. 3 shows salmeterol inhibition of histamine induced PPE.
Figure 4A:
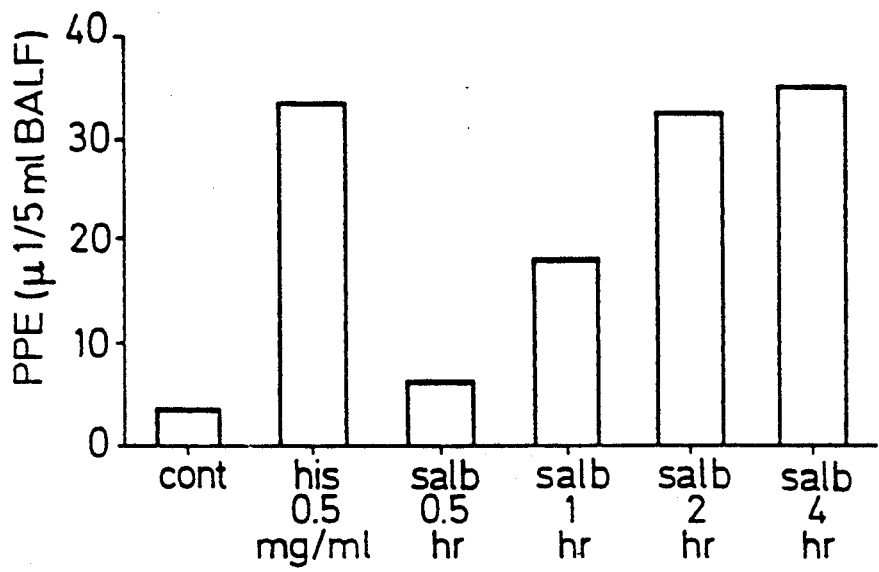
FIG. 4A and FIG. 4B show the duration of inhibition of histamine induced plasma protein extravasation in guinea pig lung by inhaled salbutamol.
Figure 4B:
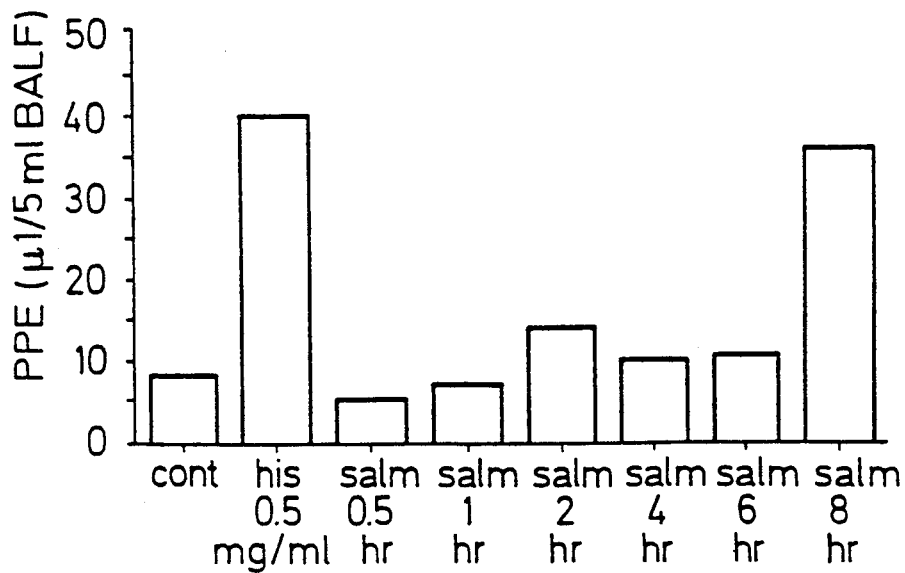

Salmeterol (nebuliser concentration: $0.001-1$ mg.$ml^{-1}$) inhibited histamine-induced PPE in a concentration-related manner, the highest doses causing complete inhibition (FIG. 3). The concentration of salmeterol require to reduce histamine-induced PPE by 50% ($ED_{50}$) was 0.015 mg.$ml^{-1}$.

Salbutamol ($0.01-1$ mg.$kg^{-1}$p.o.), 30 min prior to histamine, also caused a dose-related inhibition of PPE, the $ED_{50}$ being 0.02 mg.$kg^{-1}$.

Inhibition of histamine induced PPE by inhaled salmeterol was long-lasting, still being evident 6–8 hours after administration. In contrast, at equi-effective doses, salbutamol had a shorter duration of action, with substantial loss of activity after 2 hours

EXAMPLE 2

Anti-Inflammatory Activity in the Skin

(i) Granulocyte accumulation

The effect of $\beta_2$-adrenoreceptor agonists on granulocyte accumulation in guinea-pig skin was evaluated using a modification of the technique Issekutz et al *Lab.Invest.*, 42, 310–317 (1980).

Guinea-pig peritoneal neutrophils (PMN), elicited by glycogen (0.1% w/v), were harvested by centrifugation on histopaque 1077. PMN cells were washed in heparinised Tyrode's solution and incubated with [111]indium oxide (150 $\mu Ci$) for 15 min. Labelled PMN cells were then injected by the intracardiac route into guinea-pigs (male, Dunkin Hartley 250–350 g). Intradermal injections of a suspension of zymosan (Sigma Ltd.) in saline, or saline alone, were carried out on the ventral surface of the abdomen of each animal. After 4 hours, a blood sample and a full thickness biopsy of the injection sites were taken. The radioactivity in the blood, plasma and skin biopsies was determined. The PMN cell content of each site was then calculated.

Zymosan (0.06–2 mg.site$^{-1}$) caused a dose-related increase in PMN cell accumulation in the dermis and sub-cutaneous tissue of the injection sites. The presence of granulocytes was confirmed by histology.

Salmeterol (10 mg.kg$^{-1}$ p.o.), given 1 h before challenge, reduced zymosaninduced PMN cell accumulation. This inhibition of the response to zymosan (0.2 mg.site$^{-1}$) was dose dependent over the range of 0.1–10 mg.kg$^{-1}$ p.o. (Table 1). In contrast, salbutamol (10–100 mg.kg$^{-1}$ p.o.) had no significant inhibitory effect on PMN cell accumulation in guinea-pig skin under these conditions.

Intradermal administration of salmeterol (1–10 nmol.-site$^{-1}$), together with zymosan (0.2 mg.site$^{-1}$), also caused a significant inhibition of PMN cell accumulation.

TABLE 1

Effect of salmeterol on zymosan-induced PMN cell accumulation in guinea-pig skin

| Route | Dose | % Inhibition of PMN cell accumulation |
| --- | --- | --- |
| oral | 1.0 | 27 |
| (mg.kg$^{-1}$) | 10.0 | 59 |
| Intradermal | 10$^{-9}$ | 16 |
| (nmol.site$^{-1}$) | 10$^{-8}$ | 51 |

(ii) Vascular permeability

The effect of $\beta_2$-adrenoreceptor agonists on granulocyte-dependent and independent vascular permeability induced in guinea-pig skin, by intradermal challenge with zymosan and histamine respectively, was evaluated using a modification of the method of Issekutz *Lab. Invest.*, 45, 435–441 (1981).

Briefly, iodinated human serum albumin (10μCi) was given by intracardiac injection to guinea-pigs (male, Dunkin Hartley, 250–350 g) followed by intradermal injections into the ventral surface of the abdomen of each animal of zymosan suspension in saline, histamine, or saline alone. After 30 min (histamine) or four hours (zymosan), a blood sample and a full thickness biopsy of each injection site was taken. The radioactivity in the blood, plasma and skin biopsies was then determined. Plasma protein extravasation (PPE) was calculated as μl plasma equivalents.

Zymosan (0.06–2 mg.site$^{-1}$) caused a dose-related increase in granulocyte-dependent PPE in the skin.

Salmeterol (0.1–10 mg.kg$^{-1}$ p.o.), given 1 hour before zymosan (0.2 mg,site$^{-1}$), resulted in a statistically significant, dose-dependent reduction in PPE (Table 2). In contrast, salbutamol 10–100 mg.kg$^{-1}$ p.o.) had no inhibitory effect on zymosan-induced PPE in guinea-pig skin.

Intradermal injection of salmeterol (1–10 nmol.-site$^{-1}$) also caused a significant inhibition of granulocyte-dependent PPE when co-administered with zymosan.

TABLE 2

Effect of salmeterol on plasma protein extravasation (PPE) in guinea-pig skin

| Route | Dose | Zymosan-induced Granulocyte-dependent PPE | Histamine-induced Granulocyte independent PPE |
| --- | --- | --- | --- |
| Oral | 1.0 | 47.0 | 9.2 |
| (mg.kg$^{-1}$) | 10.0 | 56.0 | 58.5 |
| Intradermal | 10$^{-9}$ | 1.8 | NT |
| (nmol.site$^{-1}$) | 10$^{-8}$ | 51.7 | NT |

Salmeterol (10 mg.kg$^{-1}$ p.o.), administered 1 hour before histamine (100 ng.site$^{-1}$), also inhibited granulocyte-independent plasma protein extravasation in guinea-pig skin. Approximately 10-fold greater doses of salbutamol were required to achieve a comparable effect.

We claim:

1. A method of treatment of a mammal, including man, suffering from the late asthmatic reaction which comprises administering an effective amount of 4-hydroxy-α$^1$-[[[6-(4-phenylbutoxy)hexyl]amino]methyl]-1,3-benzenedimethanol or a physiologically acceptable salt or solvate thereof.

2. A method of treatment of a mammal, including man, suffering from late-phase asthma which comprises administering an effective amount of 4-hydroxy-α$^1$-[[[6-(4-phenylbutoxy)hexyl]amino]-methyl]-1,3-benzenedimethanol or a physiologically acceptable salt or solvate thereof.

3. A method of treatment according to any one of claims 1 or 2 which comprises administering an effective amount of 4-hydroxy-α$^1$-[[[6-(4-phenylbutoxy)hexyl]amino]methyl]-1,3-benzenedimethanol, 1-hydroxy-2-naphthalene-carboxylate salt.

* * * * *

Disclaimer and Dedication 5,290,815—Malcolm Johnson, Orwell: Clifford J. Whelan, Buntingford, both of England. TREATMENT OF INFLAMMATION AND ALLERGY. Patent dated Mar. 1, 1994. Disclaimer filed May 3, 2004, by the assignee, Glaxo Group Limited.

Hereby enters this disclaimer to claims 1, 2 and 3, of said patent and dedicate to the public the entire term of said patent.

*(Official Gazette, August 17, 2004)*